(12) United States Patent
Flanagan

(10) Patent No.: US 12,576,220 B2
(45) Date of Patent: Mar. 17, 2026

(54) DEVICES, SYSTEMS AND METHODS FOR IMPROVED RADIOTHERAPY EFFICACY

(71) Applicant: Boston Scientific Scimed, Inc., Maple Grove, MN (US)

(72) Inventor: Aiden Flanagan, Galway (IE)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1165 days.

(21) Appl. No.: 17/078,188

(22) Filed: Oct. 23, 2020

(65) Prior Publication Data

US 2021/0121644 A1     Apr. 29, 2021

Related U.S. Application Data

(60) Provisional application No. 62/926,044, filed on Oct. 25, 2019.

(51) Int. Cl.
| | |
|---|---|
| *A61M 13/00* | (2006.01) |
| *A61M 1/16* | (2006.01) |
| *A61M 25/00* | (2006.01) |
| *A61N 5/10* | (2006.01) |

(52) U.S. Cl.
CPC .......... *A61M 13/00* (2013.01); *A61M 1/1698* (2013.01); *A61M 25/00* (2013.01); *A61N 5/10* (2013.01); *A61M 2202/0208* (2013.01); *A61N 2005/1098* (2013.01)

(58) Field of Classification Search
CPC .. A61M 1/1678; A61M 1/1698; A61M 1/262; A61M 1/1694
See application file for complete search history.

(56) References Cited

U.S. PATENT DOCUMENTS

| | | | | |
|---|---|---|---|---|
| 4,576,590 A | * | 3/1986 | Fiddian-Green | .... A61M 1/1678 604/500 |
| 4,631,053 A | * | 12/1986 | Taheri | ................. A61M 1/1678 604/6.14 |

(Continued)

FOREIGN PATENT DOCUMENTS

| | | | | |
|---|---|---|---|---|
| CN | 112244959 A | * | 1/2021 | |
| WO | WO-02076530 A1 | * | 10/2002 | .......... A61M 1/1678 |
| WO | 2013078235 A1 | | 5/2013 | |

OTHER PUBLICATIONS

Wu, L., et al., "Tumor Size is an Independent Prognostic Factor for Stage I Ovarian Clear Cell Carcinoma: A Large Retrospective Cohort Study of 1,000 Patients", Frontiers in Oncology, vol. 12—2022 (2022) (www.frontiersin.org/journals/oncology/articles/10.3389/fonc.2022.862944) (Year: 2022).*

(Continued)

*Primary Examiner* — Bhisma Mehta
*Assistant Examiner* — Adam J. Cermak
(74) *Attorney, Agent, or Firm* — Seager, Tufte & Wickhem LLP

(57) ABSTRACT

The present disclosure relates generally to the field of medical devices. In particular, the present disclosure relates to devices, systems and methods for improved efficacy of radiotherapy treatment of hypoxic tumors. For example, the disclosed devices, systems and methods may statically or continuously oxygenate hypoxic tumors immediately prior to or simultaneous with irradiation.

20 Claims, 9 Drawing Sheets

(56) References Cited

U.S. PATENT DOCUMENTS

| 4,671,287 | A | * | 6/1987 | Fiddian-Green | ............................ A61M 25/0127 600/363 |
|---|---|---|---|---|---|
| 4,770,852 | A | * | 9/1988 | Takahara | ................ B01D 69/02 210/500.36 |
| 4,791,054 | A | * | 12/1988 | Hamada | ................ F28F 21/062 422/46 |
| 4,911,689 | A | * | 3/1990 | Hattler | ................ A61M 1/1678 604/6.14 |
| 4,986,809 | A | * | 1/1991 | Hattler | ................. A61M 1/262 623/1.1 |
| 5,037,383 | A | * | 8/1991 | Vaslef | ................. A61M 1/1678 604/500 |
| 5,271,743 | A | * | 12/1993 | Hattler | .................... B01D 65/08 604/26 |
| 5,376,069 | A | * | 12/1994 | Hattler | ................ A61M 1/1678 604/509 |
| 5,501,663 | A | * | 3/1996 | Hattler | ................ A61M 1/1678 261/DIG. 28 |
| 5,865,789 | A | * | 2/1999 | Hattler | ................ A61M 1/1678 604/101.05 |
| 6,030,358 | A | * | 2/2000 | Odland | .................... A61M 1/26 604/27 |
| 6,338,727 | B1 | * | 1/2002 | Noda | ......................... A61P 7/12 604/113 |
| 6,454,997 | B1 | * | 9/2002 | Divino, Jr. | .......... A61M 1/3621 604/4.01 |
| 6,702,783 | B1 | * | 3/2004 | Dae | ........................... A61F 7/12 604/113 |
| 6,929,618 | B1 | * | 8/2005 | Johansson | .......... A61B 5/14528 604/4.01 |
| 7,105,151 | B2 | * | 9/2006 | Unger | .................. A61K 47/544 424/9.51 |
| 7,172,727 | B2 | * | 2/2007 | Patterson | .......... B01F 23/23413 604/6.14 |
| 7,641,853 | B2 | * | 1/2010 | Cattaneo | ................ A61M 1/262 604/26 |
| 8,734,382 | B2 | * | 5/2014 | Frankowski | ........ A61M 1/1678 604/23 |
| 2001/0016729 | A1 | * | 8/2001 | Divino, Jr. | .......... A61M 1/3623 604/525 |
| 2005/0119588 | A1 | * | 6/2005 | Model | ................ A61M 1/1678 600/581 |
| 2006/0015065 | A1 | * | 1/2006 | Kumazaki | .......... A61M 1/3613 604/101.04 |
| 2006/0264810 | A1 | * | 11/2006 | Hattler | .................... B01D 63/02 604/26 |
| 2014/0343348 | A1 | * | 11/2014 | Kaplan | ................ A61M 5/158 604/21 |
| 2016/0235902 | A1 | * | 8/2016 | Flanagan | ............ A61M 1/1678 |
| 2017/0246370 | A1 | * | 8/2017 | Chen | ...................... A61M 1/285 |
| 2019/0314567 | A1 | * | 10/2019 | Straube | ............... A61M 1/1678 |
| 2020/0391007 | A1 | * | 12/2020 | Vogt | .................... A61B 17/8855 |
| 2021/0386919 | A1 | * | 12/2021 | Amin | ................... A61M 1/1678 |
| 2022/0370703 | A1 | * | 11/2022 | Khoshnejad | ........ A61M 1/3606 |

OTHER PUBLICATIONS

Li et al., "Advanced nanomaterials targeting hypoxia to enhance radiotherapy" International Journal of Nanomedicine 2018:13 5925-5936.

Hompland et al., "Combined MR Imaging of Oxygen Consumption and Supply Reveals Tumor Hypoxia and Aggressiveness in Prostate Cancer Patients" Cancer Res; 78(16) Aug. 15, 2018.

Moulder JE, Rockwell S. Hypoxic fractions of solid tumors: experimental techniques, methods of analysis, and a survey of existing data. Int J Radiat Oncol Biol Phys. May 1984;10(5):695-712. doi: 10.1016/0360-3016(84)90301-8. PMID: 6735758.

Moulder JE, Rockwell S. Tumor hypoxia: its impact on cancer therapy. Cancer Metastasis Rev. 1987;5(4):313-41. doi: 10.1007/ BF00055376. PMID: 3552280.

Rockwell S, Moulder JE. Hypoxic fractions of human tumors xenografted into mice: a review. Int J Radiat Oncol Biol Phys. Jul. 1990;19(1):197-202. doi: 10.1016/0360-3016(90)90154-c. PMID: 2143178.

Rockwell S. Oxygen delivery: implications for the biology and therapy of solid tumors. Oncol Res. 1997;9(6-7):383-90. PMID: 9406244.

Dendy, P P, and P Wardman. "Hypoxia in biology and medicine: the legacy of L H Gray." The British journal of radiology vol. 79,943 (2006): 545-9. doi:10.1259/bjr/13634453.

Ljungkvist, Anna S E et al. "Dynamics of tumor hypoxia measured with bioreductive hypoxic cell markers." Radiation research vol. 167,2 (2007): 127-45. doi:10.1667/rr0719.1.

Evans, Sydney M et al. "Comparative measurements of hypoxia in human brain tumors using needle electrodes and EF5 binding." Cancer research vol. 64,5 (2004): 1886-92. doi:10.1158/0008-5472. can-03-2424.

Nordsmark, Marianne et al. "Prognostic value of tumor oxygenation in 397 head and neck tumors after primary radiation therapy. An international multi-center study." Radiotherapy and oncology : journal of the European Society for Therapeutic Radiology and Oncology vol. 77,1 (2005): 18-24. doi:10.1016/j.radonc.2005.06. 038.

Isa, A Y et al. "Hypoxia in head and neck cancer." The British journal of radiology vol. 79,946 (2006): 791-8. doi:10.1259/bjr/ 17904358.

Wilson GD. "Hypoxia and prognosis: the oxygen tension mounts" [Frontiers in Bioscience 2007;12:3502-3518.

Vaupel, Peter, and Arnulf Mayer. "Hypoxia in cancer: significance and impact on clinical outcome." Cancer metastasis reviews vol. 26,2 (2007): 225-39. doi:10.1007/s10555-007-9055-1.

Okunieff, Paul et al. "Past, present, and future of oxygen in cancer research." Advances in experimental medicine and biology vol. 566 (2005): 213-22. doi:10.1007/0-387-26206-7_29.

Foo, Serene S et al. "Functional imaging of intratumoral hypoxia." Molecular imaging and biology vol. 6,5 (2004): 291-305. doi:10. 1016/j.mibio.2004.06.007.

Brown, J Martin, and William R Wilson. "Exploiting tumour hypoxia in cancer treatment." Nature reviews. Cancer vol. 4,6 (2004): 437-47. doi:10.1038/nrc1367.

Tatum, James L et al. "Hypoxia: importance in tumor biology, noninvasive measurement by imaging, and value of its measurement in the management of cancer therapy." International journal of radiation biology vol. 82,10 (2006): 699-757. doi:10.1080/ 09553000601002324.

Moeller, Benjamin J et al. "Hypoxia and radiotherapy: opportunities for improved outcomes in cancer treatment." Cancer metastasis reviews vol. 26,2 (2007): 241-8. doi:10.1007/s10555-007-9056-0.

Kaufman, Bennett et al. "Proceedings of the Oxygen Homeostasis/ Hypoxia Meeting." Cancer research vol. 64,9 (2004): 3350-6. doi:10.1158/0008-5472.can-03-2611.

Vaupel, Peter. "Tumor microenvironmental physiology and its implications for radiation oncology." Seminars in radiation oncology vol. 14,3 (2004): 198-206. doi:10.1016/j.semradonc.2004.04.008.

Evans, S M et al. "Detection of hypoxia in human squamous cell carcinoma by EF5 binding." Cancer research vol. 60,7 (2000): 2018-24.

International Search Report and Written Opinion for the International Patent Application No. PCT/US2020/056965, mailed Jan. 26, 2021, 28 pages.

* cited by examiner

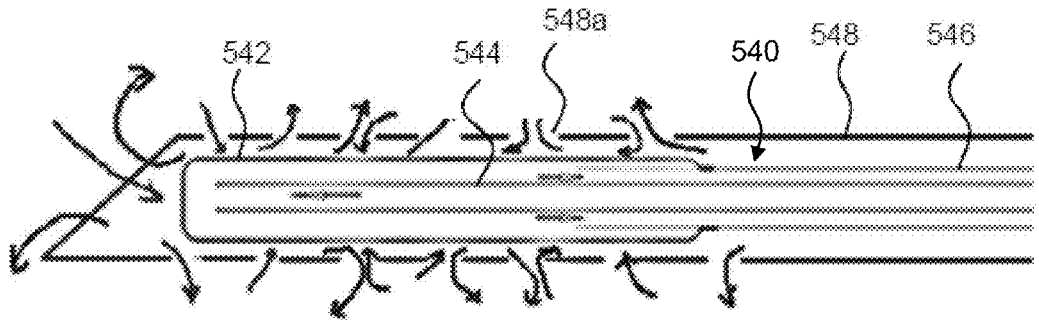
FIG. *5E*
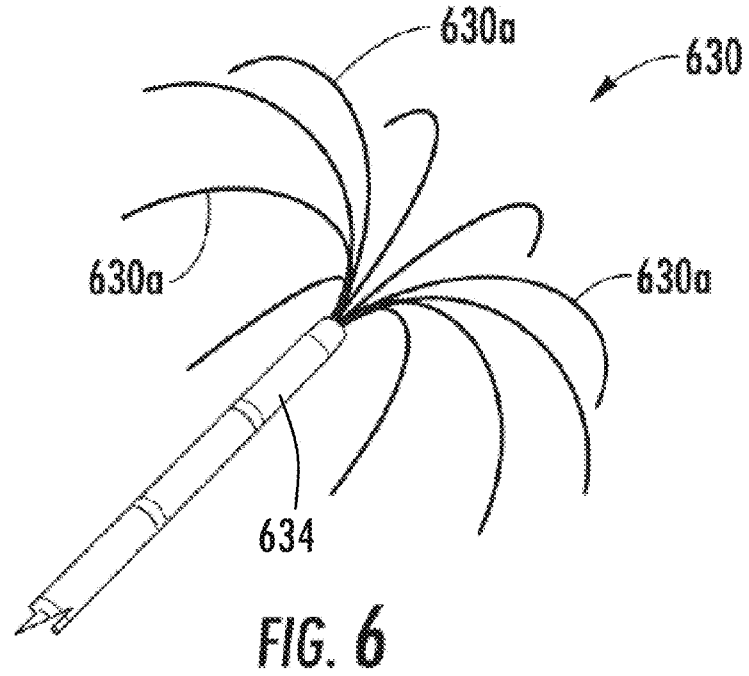
FIG. 6

730

730

730

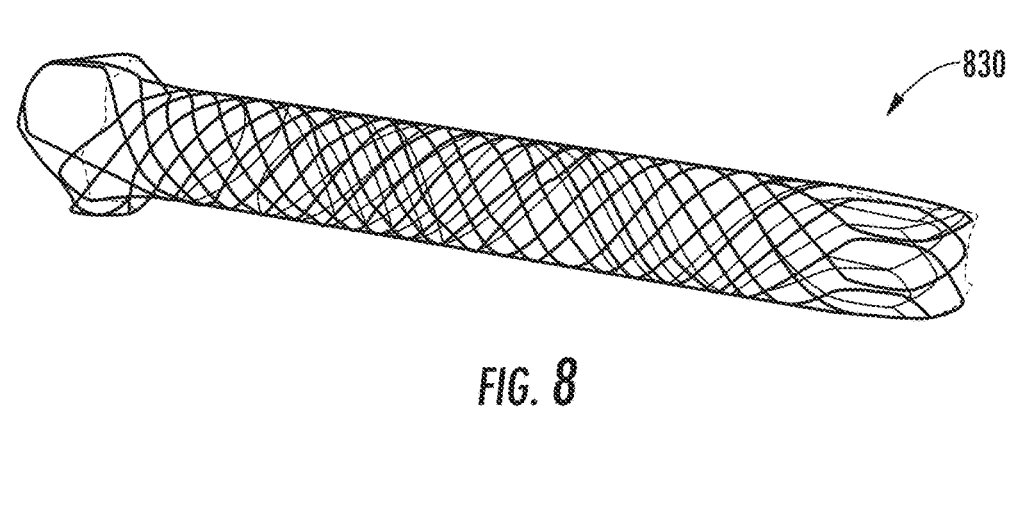
*FIG. 8*
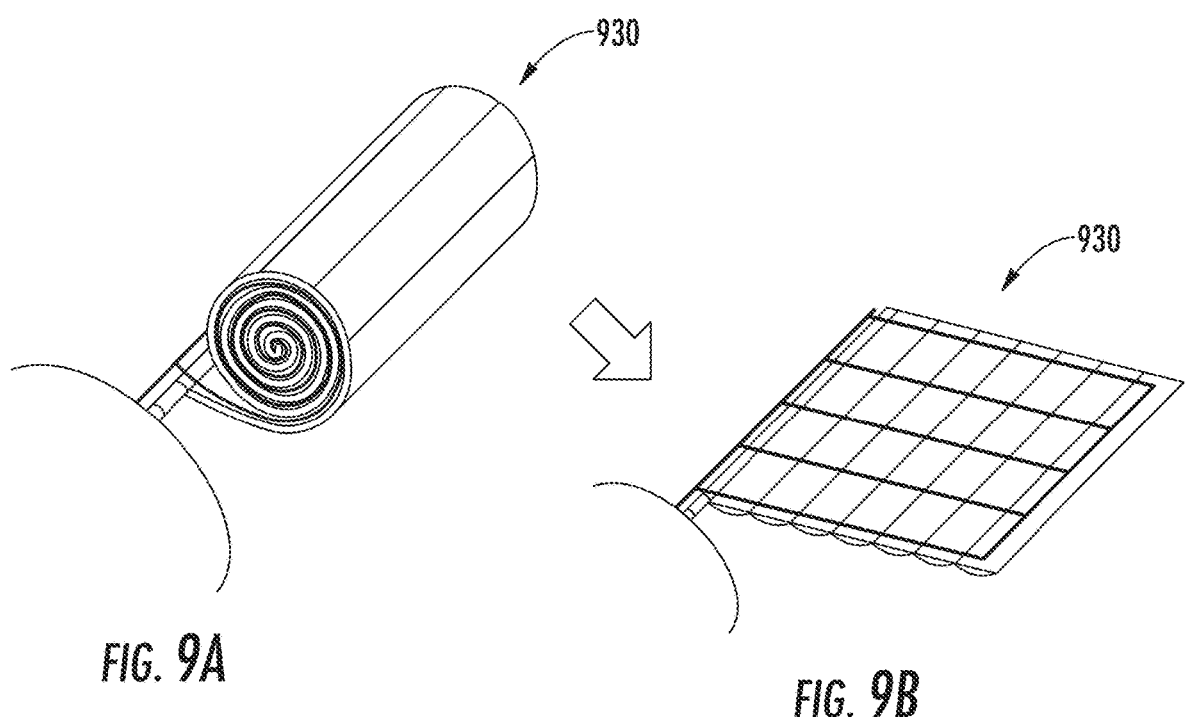
*FIG. 9A*
*FIG. 9B*

930

TM-1000__0876          2016/07/13  10:37  L    x600     100 um

DEVICES, SYSTEMS AND METHODS FOR IMPROVED RADIOTHERAPY EFFICACY

CROSS-REFERENCE TO RELATED APPLICATION

This application claims the benefit of U.S. Provisional Application No. 62/926,044, filed Oct. 25, 2019 and entitled "DEVICES, SYSTEMS AND METHODS FOR IMPROVED RADIOTHERAPY EFFICACY", the disclosure of which is hereby incorporated by reference in its entirety.

FIELD

The present disclosure relates generally to the field of medical devices. In particular, the present disclosure relates to devices, systems and methods for improved efficacy of radiotherapy treatment of hypoxic tumors.

BACKGROUND

Radiotherapy has been used as a treatment for various cancers for decades. It is well established that hypoxia influences the efficacy of radiotherapy treatment of cancerous tumors, including large/bulky tumors with extensive necrosis, small primary and recurrent tumors, micro-metastases and surgical margins with microscopic tumor involvement. Tumors tend to be to be highly vascularized and fast growing as compared to normal/healthy cells. Vascularization is haphazard: vessels can collapse and there is widespread shunting (blood bypasses from arteries into veins avoiding capillary bed), which stops oxygen from getting to the tumor cells, causing hypoxic zones in the tumor. This limits the amount of oxygen available to be converted to oxygen-derived free radicals upon exposure to ionizing radiation. In vitro animal trials have demonstrated that hypoxic cancer cells are approximately three times more resistant to the effects of radiotherapy than aerobic cancer cells (FIG. 1).

A variety of advantageous medical outcomes may therefore be realized by the medical devices, systems and methods of the present disclosure.

SUMMARY

In some aspects, the present disclosure is directed to medical systems that comprise (a) a flexible elongate member, (b) an oxygenation element fluidly connected to a proximal end of the flexible elongate member, (c) a gas exchange device fluidly connected to a distal end of the flexible elongate member, and (d) a gas exchange fluid contained within the system and flowable from the oxygenation element to the gas exchange device through a first lumen of the flexible elongate member and flowable from the gas exchange device to the oxygenation element through a second lumen of the flexible elongate member.

In some embodiments, the proximal end of the first lumen is fluidly connected to a gas exchange fluid outlet port of the oxygenation element, a distal end of the first lumen is fluidly connected to the gas exchange device, a proximal end of the second lumen is fluidly connected to a gas exchange fluid inlet port of the oxygenation element, and a distal end of the second lumen is fluidly connected to the gas exchange device.

In some embodiments, which can be used in conjunction with the above aspects and embodiments, the oxygenation element includes an oxygen inlet port and an oxygen outlet port.

In some embodiments, which can be used in conjunction with the above aspects and embodiments, the gas exchange device is configured to deliver oxygen from the gas exchange fluid to a hypoxic tumor of a patient.

In some embodiments, which can be used in conjunction with the above aspects and embodiments, the systems further comprise a gas exchange membrane disposed within the oxygenation element, the gas exchange membrane configured to transfer oxygen to the gas exchange fluid. In some of these embodiments, the first lumen of the flexible elongate member is configured to deliver the oxygenated gas exchange fluid from the oxygenation element to the gas exchange device. In some of these embodiments, the second lumen of the flexible elongate member is configured to deliver the gas exchange fluid from the gas exchange device to the oxygenation element. In some of these embodiments, the gas exchange device comprises a needle that comprises an outer tubular member, an inner tubular member disposed within the outer tubular member, and the gas exchange membrane is disposed at a distal end of the outer tubular member and, optionally, an outer sheath having porous sides and an open or closed distal end. Where such an outer sheath is provided, a fluid such as normal saline or another suitable fluid may be pumped through a space between the outer sheath and the outer tubular member, thereby assisting mass transport of oxygen to surrounding tissue (in some cases, the fluid is pumped through the space between the outer sheath and outer tubular member in a pulsating fashion).

In some embodiments, which can be used in conjunction with the above aspects and embodiments, the gas exchange device includes a first configuration and a second configuration, and a surface area of the second configuration is greater than the surface area of the first configuration.

In other aspects, the present disclosure is directed to methods that comprise: (a) positioning a gas exchange device (for example, a gas exchange in accordance with the above aspects and embodiments, among others) within or adjacent to a hypoxic tumor of a patient, (b) delivering oxygen from the gas exchange device to the hypoxic tumor such that some or all of the cells of the hypoxic tumor become hyperoxic, and (c) irradiating the tumor.

In some embodiments, the methods further comprise, prior to positioning the gas exchange device, identifying one or more hypoxic regions of the tumor. In some of these embodiments, the hypoxic region is identified using magnetic resonance imaging.

In some embodiments, which can be used in conjunction with the above aspects and embodiments, the methods further comprise cooling the gas exchange device while delivering oxygen to the hypoxic tumor.

In some embodiments, which can be used in conjunction with the above aspects and embodiments, the methods further comprise removing the gas exchange device from the patient after irradiating the tumor.

In some embodiments, which can be used in conjunction with the above aspects and embodiments, the methods further comprise delivering another dose of oxygen from the gas exchange device to the tumor and irradiating the tumor a second time.

In some aspects, the present disclosure is directed to medical systems that comprise (a) a flexible catheter, (b) an external gas exchange device fluidly connected to a proximal end of the catheter, (c) an internal gas exchange device fluidly connected to a distal end of the catheter, and (d) a gas exchange fluid contained within the system and flowable from the external gas exchange device to the internal gas exchange device through a first channel of the catheter and flowable from the internal gas exchange device to the external gas exchange device through a second channel of the catheter.

In some embodiments, a proximal end of the first channel is fluidly connected to a gas exchange fluid outlet port of the external gas exchange device, a distal end of the first channel is fluidly connected to the internal gas exchange device, a proximal end of the second channel is fluidly connected to a gas exchange fluid inlet port of the external gas exchange device, and a distal end of the second channel is fluidly connected to the internal gas exchange.

In some embodiments, which can be used in conjunction with the above aspects and embodiments, the external gas exchange device includes an oxygen inlet port and an oxygen outlet port.

In some embodiments, which can be used in conjunction with the above aspects and embodiments, the internal gas exchange device is configured to deliver oxygen from the gas exchange fluid to a hypoxic tumor of a patient.

In some embodiments, which can be used in conjunction with the above aspects and embodiments, the systems further comprise a gas exchange membrane disposed within the external gas exchange device, the gas exchange membrane configured to transfer oxygen to the gas exchange fluid.

In some embodiments, which can be used in conjunction with the above aspects and embodiments, the first channel of the catheter is configured to deliver the oxygenated gas exchange fluid from the external gas exchange device to the internal gas exchange device.

BRIEF DESCRIPTION OF THE DRAWINGS

Non-limiting embodiments of the present disclosure are described by way of example with reference to the accompanying figures, which are schematic and not intended to be drawn to scale. In the figures, each identical or nearly identical component illustrated is typically represented by a single numeral. For purposes of clarity, not every component is labeled in every figure, nor is every component of each embodiment shown where illustration is not necessary to allow those of ordinary skill in the art to understand the disclosure. In the figures:

FIGS. 3-9C provide perspective views of various gas exchange devices, according to various embodiments of the present disclosure.

DETAILED DESCRIPTION

The present disclosure is not limited to the particular embodiments described herein. The terminology used herein is for the purpose of describing particular embodiments only, and is not intended to be limiting beyond the scope of the appended claims. Unless otherwise defined, all technical terms used herein have the same meaning as commonly understood by one of ordinary skill in the art to which the disclosure belongs.

As used herein, the singular forms "a," "an," and "the" are intended to include the plural forms as well, unless the context clearly indicates otherwise. It will be further understood that the terms "comprises" and/or "comprising," or "includes" and/or "including" when used herein, specify the presence of stated features, regions, steps, elements and/or components, but do not preclude the presence or addition of one or more other features, regions, integers, steps, operations, elements, components and/or groups thereof.

As used herein, the term "distal" refers to the end farthest away from the medical professional or physician when introducing a device into a patient, while the term "proximal" refers to the end closest to the medical professional or physician when introducing a device into a patient.

Clinical studies using oxygen microelectrodes, magnetic resonance imaging (MRI), electron paramagnetic resonance (EPR), immunohistochemical detection of exogenous and/or endogenous molecular markers of cellular hypoxia and other noninvasive imaging techniques have all demonstrated that hypoxia is a common feature of tumors in patients presenting for therapy. Because the underlying chemical reactions required to generate oxygen-derived free radicals are completed within milliseconds of irradiation, oxygen must be present during irradiation to provide full radiosensitization of the tumor. The presence of oxygen before or after irradiation is irrelevant to achieving full radiosensitization. Laboratory studies and clinical trials attempting to circumvent the resistance to radiotherapy induced by hypoxia (including blood substitutes, vasodilators, increased hematocrit levels, hemoglobin binding affinity reduction, hyperbaric oxygen/carbon dioxide, oxygen mimetics, hypoxic cell targeting drugs, etc.) have been unsuccessful due to problems associated with lack of functional vascularization, practical implementation, toxicity and/or variable results.

In various embodiments, the present disclosure relates to devices, systems and methods to efficiently and effectively deliver oxygen to hypoxic tumors so that the cells of the tumor range from somewhat less than normoxic up to hyperoxic during the radiotherapy session to increase the efficacy of the radiotherapy treatment. For example, the oxygen level may be increased so that the oxygen partial pressure is greater than 10 mm Hg, greater than 20 mm Hg, greater than 30 mm Hg, greater than 40 mm Hg, or greater than 50 mm Hg, in some embodiments.

Figure 1:
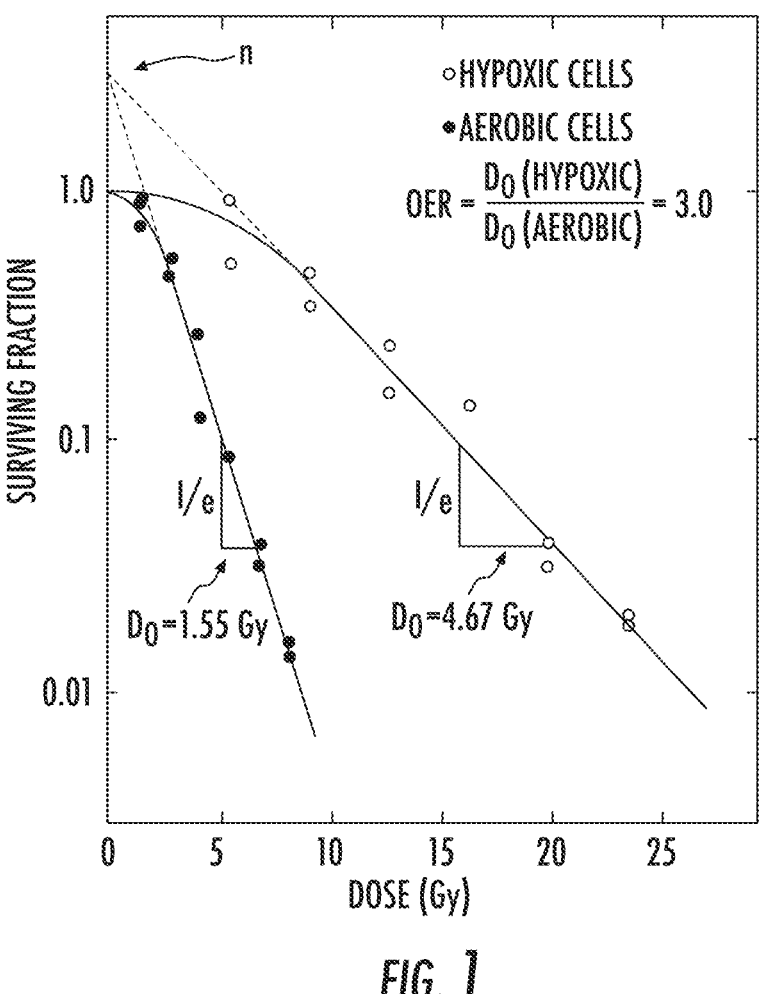
FIG. 1 compares the susceptibility of hypoxic cancer cells and aerobic cells to radiotherapy.
Figures 2A, 2B:
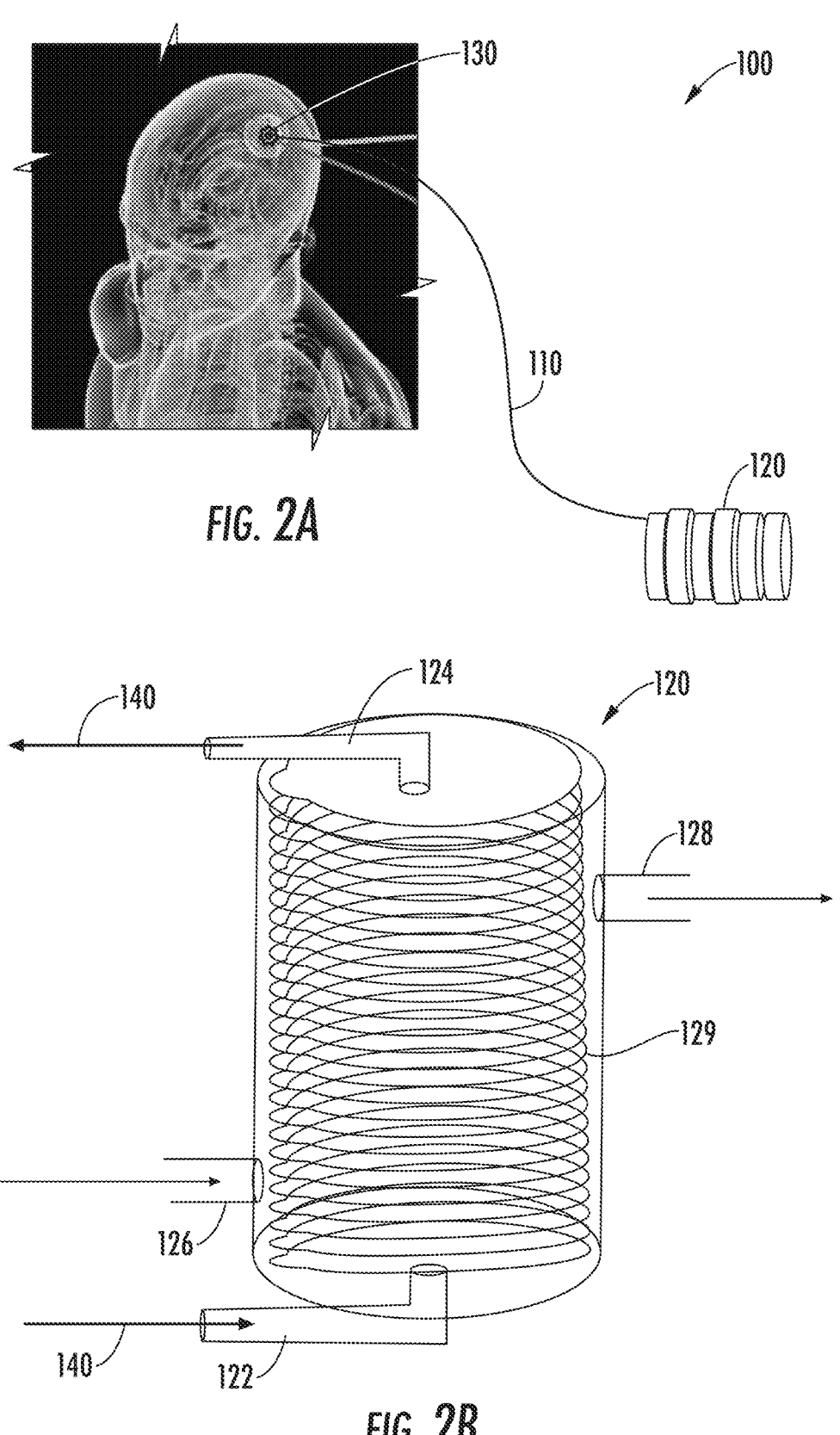
FIGS. 2A-2B provide perspective views of a medical system, according to one embodiment of the present disclosure.

Referring to FIGS. 2A-2B, in one embodiment, the present disclosure relates to a minimally invasive medical system 100 which includes circulating closed-circuit gas exchange fluid (including $O_2$ gas per se) to deliver oxygen to hypoxic regions of a tumor. The medical system 100 may include an oxygenation element 120 (e.g., external/proximal membrane gas exchange device) fluidly connected to a proximal end of a flexible elongate member 110 (e.g., catheter, etc.) and a gas exchange device 130 (e.g., internal/distal gas exchange device) fluidly connected to a distal end of the flexible elongate member 110. A gas exchange fluid 140 may be housed/contained within the medical system 100 and flowable (e.g., configured to flow/circulate) from the oxygenation element 120 to the gas exchange device 130 through a first lumen 112 (e.g., delivery lumen/channel) (see FIG. 4) of the flexible elongate member 110 and from the gas exchange device 130 to the oxygenation element 120 through a second lumen 114 (e.g., return lumen/channel) (see FIG. 4) of the flexible elongate member 110. For example, a proximal end (e.g., proximal opening) of the first lumen 112 of the flexile elongate member 110 may be fluidly connected to a gas exchange fluid outlet port 124 of the oxygenation element 120 and a distal end (e.g., distal opening) of the first lumen 112 may be fluidly connected to the gas exchange device 130. A proximal end (e.g., proximal opening) of the second lumen 114 of the flexible elongate member 110 may be fluidly connected to a gas exchange fluid inlet port 122 of the oxygenation element 120 and a distal end (e.g., distal opening) of the second lumen 114 may be fluidly connected to the gas exchange device 130.

In one embodiment, the oxygenation element 120 may include an oxygen inlet port 126 configured to deliver/introduce oxygen into the oxygenation element 120 and an oxygen outlet port 128 configured to remove the oxygen from the oxygenation element 120. In various embodiments, oxygen may be pumped into the oxygenation element 120 as a gas (e.g., air or purified oxygen) or liquid (e.g., water aerated with oxygen bubbles). A gas exchange membrane 129 may be housed within the oxygenation element 120 to transfer/deliver the oxygen flowing through the oxygenation element 120 to the circulating gas exchange fluid 140. In various embodiments, the gas exchange membrane 129 may include a high surface area (e.g., folded, pleated, coiled, etc.) to maximize the transfer of oxygen to the gas exchange fluid 140. In addition, or alternatively, the oxygenation element 120 may be pressurized to further facilitate the transfer of oxygen to the gas exchange fluid (e.g., to provide a super-saturated solution of oxygen in the gas exchange fluid).

In one embodiment, the gas exchange fluid 140 may have a high oxygen dissolution capacity (e.g., 50% dissolution) to efficiently deliver/transfer oxygen to the hypoxic tumor. For example, arterial blood may include oxygen at a partial pressure of approximately 100 mm Hg while tissues may include oxygen at a partial pressure lower than 100 mm Hg according to the distance from the capillaries. This difference in partial pressures drives the diffusion of oxygen from the blood into the tissues. By comparison, the gas exchange fluid 140 may include oxygen at a partial pressure greater than 750 mm Hg to efficiently drive diffusion of oxygen into the hypoxic tissue. In various embodiments, the patient may be placed within a hyperbaric chamber to further facilitate the transfer of oxygen from the gas exchange fluid into the hypoxic tissue. By way of non-limiting example, the gas exchange fluid 140 may include perfluorocarbon (e.g., per-fluorodecalin). In some embodiments, the gas exchange fluid may be $O_2$ gas.

In one embodiment, the gas exchange device 130 may be configured to move between a low surface area first configuration (e.g., delivery configuration) and a high surface area second configuration (e.g., deployed configuration). In various embodiments, the first configuration may allow the gas exchange device 130 to be advanced through a body lumen, body passage or tissue (e.g., housed within a delivery sheath or needle) to position the gas exchange device 130 adjacent to or within the hypoxic tumor. The second configuration may allow the gas exchange device 130 to maximize the surface area available to deliver/transfer oxygen from the gas exchange fluid 140 (e.g., when distally advanced/extended from within the delivery sheath or needle) to the hypoxic tumor. In various embodiments, as discussed in further detail below, all or a portion of the gas exchange device may include a solid and oxygen permeable membrane (e.g., silicone membrane, etc.) configured to deliver/transfer oxygen from the gas exchange fluid 140 to the hypoxic tissue.

In use, and by way of example, a flexible elongate member 110 of the present disclosure may be advanced through a body lumen, body passage or body tissue of a patient to position a gas exchange device 130 disposed along a distal end of the flexible elongate member 110 within or adjacent to a hypoxic tumor of the patient. For example, the gas exchange device 130 may be disposed in a first configuration within a penetrating member (e.g., needle, etc.) attached to a distal end of the flexible elongate member 110. The gas exchange device 130 may then be deployed from within the penetrating member to move from the first configuration to the second configuration adjacent to or within the hypoxic tumor. The oxygenated or superoxygenated gas exchange fluid 140 may then be delivered from the oxygenation element 120 to the gas exchange device 130 through the first lumen 112 of the flexible elongate member 110. Oxygen may diffuse from the gas exchange fluid 130 through a porous membrane of the gas exchange device 130 and into the hypoxic tumor to render all or substantially all of the tumor cells normoxic or hyperoxic (e.g., aerobic). The gas exchange fluid 140 may then flow (e.g., return) from the gas exchange device 130 to the oxygenation element 120 through the second lumen 114 of the flexible elongate member 110 to be reoxygenated. In various embodiments, oxygen may be delivered to the tumor statically (e.g., a single dose) or continuously (e.g., by the circulating reoxygenated gas exchange fluid). In some embodiments, a dose of ionizing radiation (e.g. via radiotherapy, irradiation, etc.) may be administered to the tumor, immediately following (e.g., within milliseconds) or simultaneously with the delivery of oxygen into the hypoxic tumor, to convert some or all of the oxygen molecules in the tumor into cell-damaging oxygen-derived free radicals. In some embodiments (e.g., in the case of brachytherapy) radiation particles (e.g., Thera-Sphere® Yttrium-90 Glass Microspheres from Biocompatibles UK Ltd, a BTG International group company) may be administered into the tissue before oxygen delivery.

In one embodiment, the gas exchange device 130 may be returned to the first configuration (e.g., retracted into the needle) and removed from the patient following the administration of ionizing radiation. Alternatively, the gas exchange device 130 may remain deployed adjacent to or within the tumor over a course of multiple days and the oxygenation element 120 reattached to the proximal end of the flexible elongate member 110 such that a series of radiotherapy sessions may be performed. For example, radiotherapy sessions may be performed once daily for five consecutive days, with oxygen delivered to the tumor immediately prior to or simultaneous with the irradiation. Between radiotherapy sessions an anoxic gas exchange fluid may be introduced into the gas exchange device 130 to act as an oxygen sink to return the tumor to a hypoxic state.

In various embodiments, one or more additional steps or actions may be taken to further facilitate diffusion of oxygen into the hypoxic tumor. For example, the patient may be placed in a hyperbaric chamber (e.g., 2X atmospheric pressure), the surface of the gas exchange device 130 may be cooled (e.g., by cooling the circulating gas exchange fluid) and/or the tissue or anatomical location surrounding/containing the tumor may be cooled (e.g., using an ice pack or other cooling device such as a cooling balloon or cryotherapeutic device). Cooling enables more oxygen to be dissolved in bodily fluid (for example, cooling to 20° C. increases solubility of $O_2$ by approximately 33% relative to body temperature). As the fluid gradually warms in the body, the effective partial pressure increases, aiding diffusion and prolonging the 02 content. In addition, or alternatively, an ultrasonic or sonic transducer and/or an impeller may be incorporated into the gas exchange device to further facilitate/drive oxygen diffusion.

In various additional embodiments, one or more specific hypoxic regions of the tumor (e.g., local areas) may be identified prior to positioning of the gas exchange device 130 within or adjacent to the tumor. For example, a magnetic resonance image, perfusion scan, ultrasonic scan and/or a miniature oxygen sensor probe (e.g., inserted into the tumor) may provide a model/map of the tumor vasculature and the gas exchange device(s) 130 positioned relative to the poorly perfused (e.g., hypoxic) zone(s) of the tumor to maximize/optimize oxygen diffusion.

Figure 3:
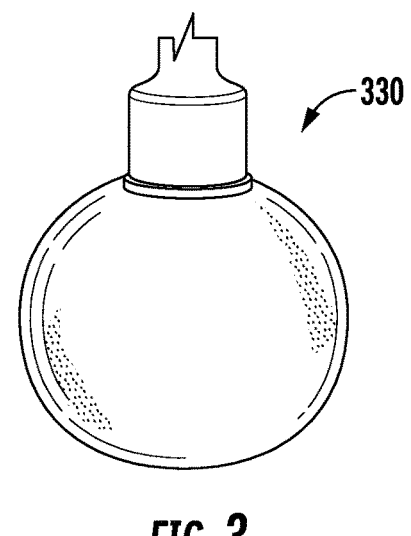

Referring to FIG. 3, in one embodiment, a gas exchange device 330 of the present disclosure may include a compliant balloon configured to move between a low surface area first configuration (e.g., delivery configuration) and a high surface area second configuration (e.g., deployed configuration). For example, once advanced from within the delivery needle and properly positioned within a hypoxic tumor (as discussed above), the gas exchange fluid 140 may be pumped/flowed into the gas exchange device 330 through the first lumen 112 of the flexible elongate member 110 to inflate the gas exchange device 330. In various embodiments, the gas exchange device may include a compliant material configured to move to a variety of different inflated configurations, e.g., based on the size/shape of the hypoxic tumor. In various embodiment, all or a portion of the gas exchange device 330 may be formed from or include a solid and oxygen permeable membrane (e.g., silicone membrane, etc.) to deliver/transfer oxygen from the gas exchange fluid 140 to the hypoxic tissue (as discussed above). Rather than continuously circulating the gas exchange fluid 140 through the gas exchange device 330, in one embodiment the gas exchange device 330 may be filled to the desired volume with the gas exchange fluid 140 and maintained at that volume to deliver oxygen into the hypoxic tumor throughout the duration of the radiotherapy treatment. In one embodiment, to further facilitate the transfer of oxygen into the hypoxic tumor, the gas exchange device 330 may be partially deflated prior to the radiotherapy treatment to provide a space between an outer surface of the gas exchange device 330 and an inner surface of the hypoxic tumor into which the oxygenated gas may accumulate and interact with interstitial fluids of the tumor.

Figure 4:
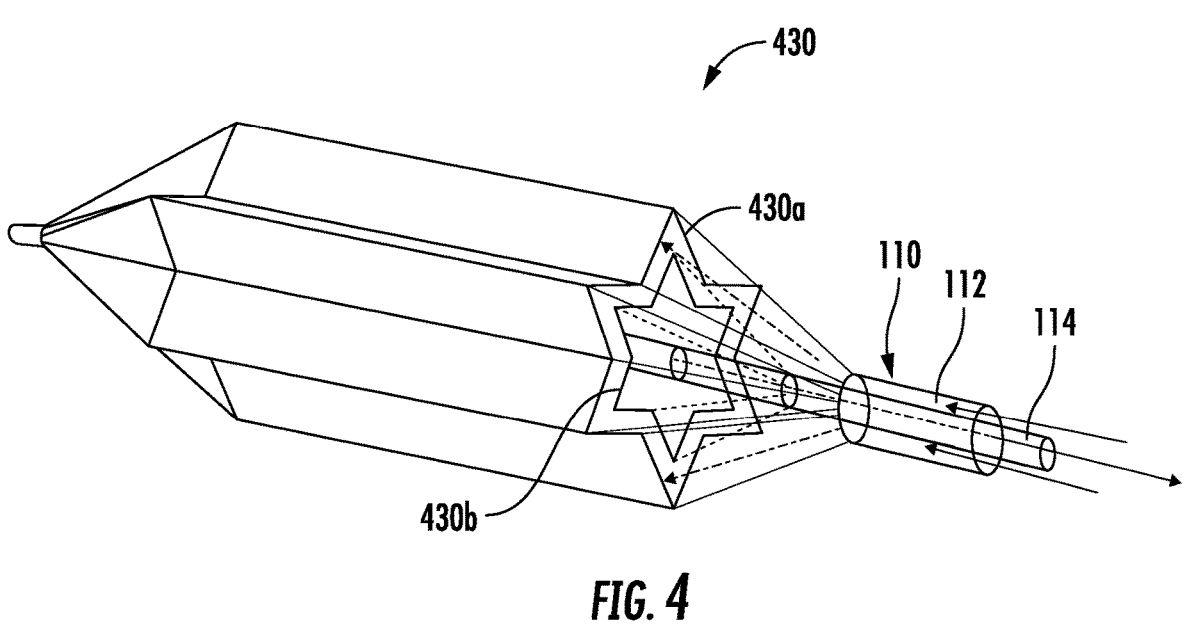

Referring to FIG. 4, in one embodiment, a gas exchange device 430 of the present disclosure may include an inner balloon 430b and outer balloon 430a configured to move between a low surface area first configuration (e.g., delivery configuration) and a high surface area second configuration (e.g., deployed configuration). In various embodiments, the gas exchange device 430 may have an irregular or undulating second configuration to maximize the surface area for oxygen transfer to the hypoxic tumor. For example, once advanced from within the delivery needle and properly positioned adjacent to or within a hypoxic tissue (as discussed above), the gas exchange fluid 140 may be pumped/flowed between the inner and outer balloons 430a, 430b of the gas exchange device 430 through the first lumen 112 of the flexible elongate member 110 to inflate the gas exchange device 430. The gas exchange fluid 140 may return to the oxygenation element 120 through the second lumen 114 running through a center of the gas exchange device 430 and through the flexible elongate member 110. In various embodiments, the gas exchange device 430 may include a compliant material such that the gas exchange device 430 may move to a variety of different inflated configurations, e.g., based on the size/shape of the hypoxic tumor. All or a portion of the gas exchange device 430 may be formed from or include a solid and oxygen permeable membrane (e.g., silicone membrane, etc.) to deliver/transfer oxygen from the gas exchange fluid 140 to the hypoxic tissue (as discussed above). In one embodiment, to further facilitate the transfer of oxygen into the hypoxic tumor, the gas exchange device 430 may be partially deflated prior to the radiotherapy treatment to provide a space between an outer surface of the gas exchange device 430 and an inner or outer surface of the hypoxic tumor into which the oxygenated gas may accumulate and interact with interstitial fluids.

Figure 5A:
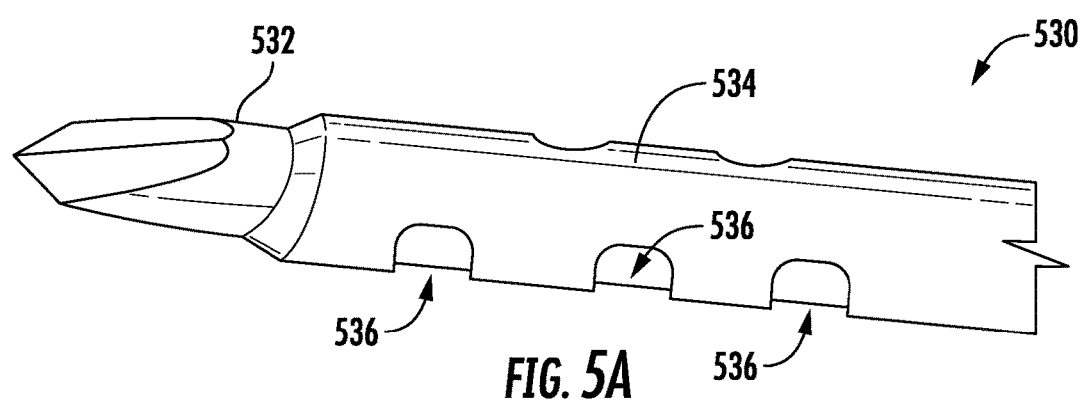

Referring to FIG. 5A, in one embodiment, a gas exchange device 530 of the present disclosure may include a trocar 532 with a tissue-penetrating tip slidably/movably disposed within an outer sheath 534. Once properly positioned adjacent to or within a hypoxic tissue (as discussed above), the trocar 532 may be removed from within the outer sheath 534 and replaced with a needle (not shown). All or a portion of the needle may be formed from or include a solid and oxygen permeable membrane (e.g., silicone membrane, etc.) to deliver/transfer oxygen from the gas exchange fluid 140 through the exit ports 536 and into the hypoxic tissue.

Figure 5B:
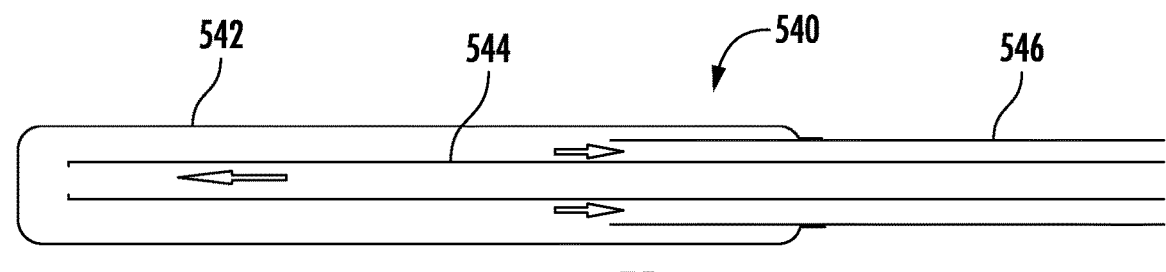

One embodiment of a needle 540 is shown in FIG. 5B, which includes an oxygen diffusing tip. Gas exchange fluid enters through an inner tubular member, for example, an inner hypotube 544 and exits through an outer tubular member, for example, an outer hypotube 546, or vice versa. An oxygen permeable membrane 542, for example, a silicone membrane, is adhered to an outside surface of the outer hypotube 546 at a distal end thereof as shown.

Figure 5C:
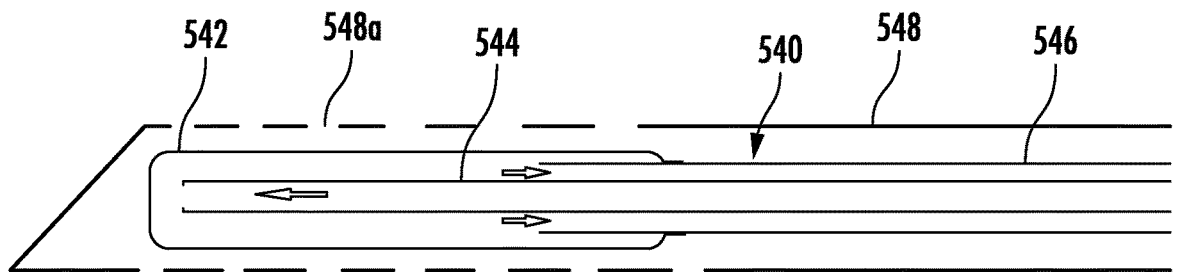

FIG. 5C illustrates a further embodiment, which includes a needle 540 like that of FIG. 5A having an oxygen diffusing tip (oxygen permeable membrane 542), inner hypotube 544 and outer hypotube 546, and also further comprises an outer sheath 548 having porous sides (including, for example, a plurality of side apertures 548a) and an open or closed distal end. During operation, the outer sheath 548 can be retracted, if desired, thereby exposing the oxygen diffusing tip 542.

Figure 5D:
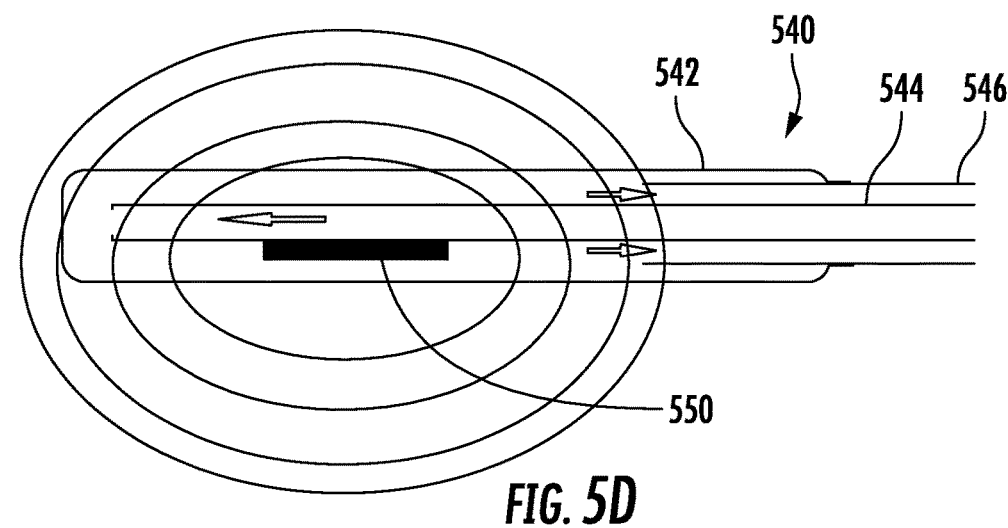

FIG. 5D illustrates a further embodiment, which includes a needle 540 like that of FIG. 5B having an oxygen diffusing tip (oxygen permeable membrane 542), inner hypotube 544 and outer hypotube 546, and which also further comprises an ultrasonic transducer 550, from which ultrasonic waves W (schematically represented by concentric ellipses) are emitted.

FIG. 5E illustrates a further embodiment, which includes a needle 540 like that of FIG. 5C having an oxygen diffusing tip (oxygen permeable membrane 542), inner hypotube 544 and outer hypotube 546, and also further comprising an outer sheath 548 having porous sides and an open or closed distal end (the distal end is open in the embodiment shown). During operation, fluid such as normal saline or another suitable fluid may be pumped through the fluid lumen between the outer sheath 548 and outer hypotube 546 thereby leading to mass transport of oxygen (advection) to surrounding tissue. In some embodiments, the fluid is pumped through the space between the outer sheath 548 and outer hypotube 546 in a pulsating fashion as indicated by arrows in FIG. 5E. Pulsations may be created, for example, by a pulsating proximal syringe connected to the fluid lumen between the outer sheath 548 and outer hypotube 546 and/or by placing a vibrating membrane within the fluid lumen. The vibrating membrane may be, for example, the oxygen permeable membrane 542 or may be a separate membrane within the fluid lumen that causes the fluid to move forward and backward (e.g. a balloon within the needle membrane).

Referring to FIG. 6, in one embodiment, a gas exchange device 630 of the present disclosure may include a plurality of needles 630*a* slidably disposed within an outer sheath 634. Once properly positioned adjacent to or within a hypoxic tissue (as discussed above), the plurality of needles 630*a* may be advanced/deployed from within the outer sheath 634 to self-deploy and penetrate various distinct/ different portions of the hypoxic tumor (e.g., to optimize spatial distribution of the needles 630*a* within the tumor). All or a portion of the needles 630*a* may be formed from or include a solid and oxygen permeable membrane (e.g., silicone membrane, etc.) to deliver/transfer oxygen from the gas exchange fluid 140 into the hypoxic tissue (as discussed above).

Figures 7A, 7B, 7C:
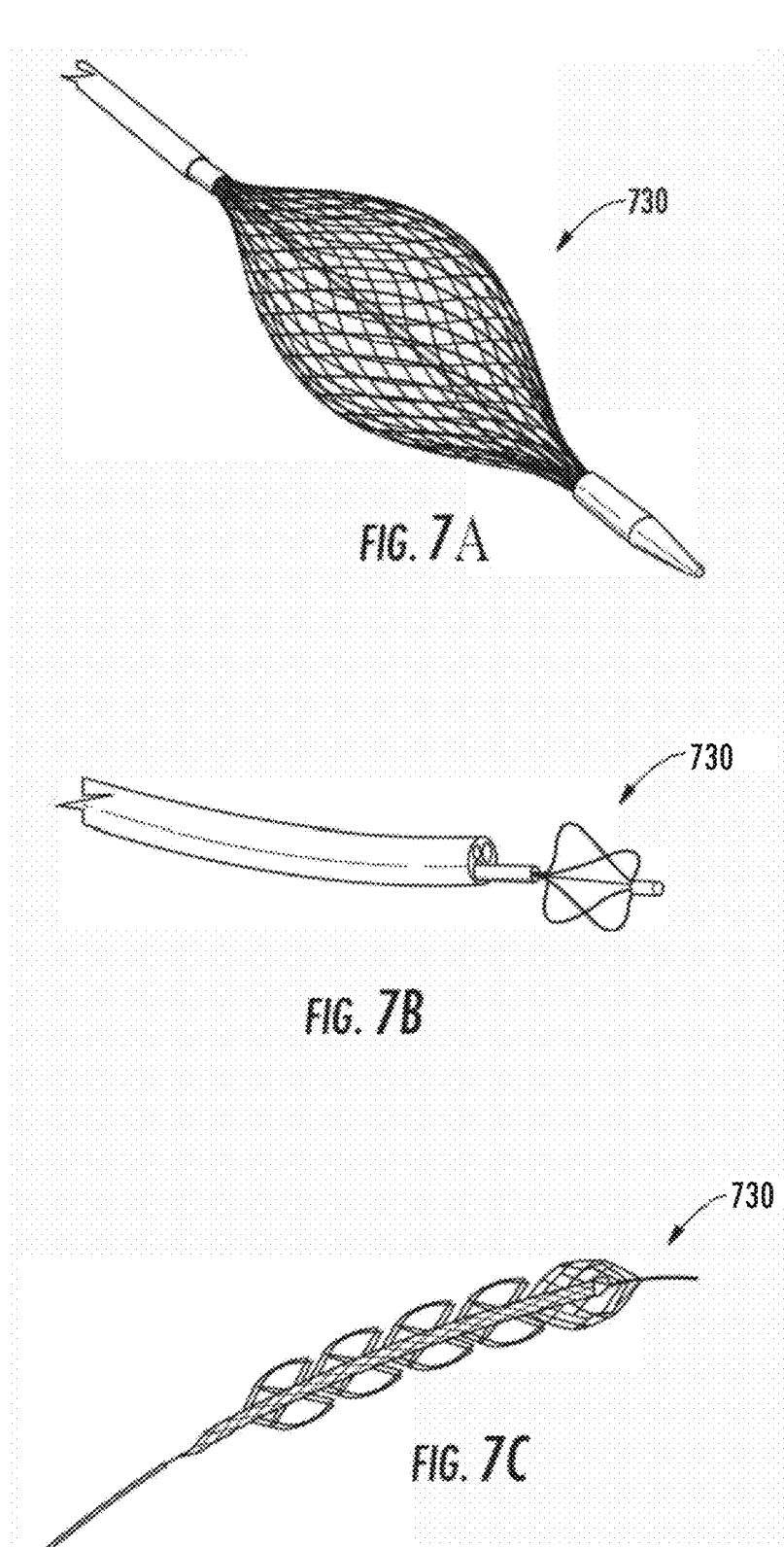

Referring to FIGS. 7A, 7B and 7C, in one embodiment, a gas exchange device 730 of the present disclosure may include a self-expanding stent framework comprising one or more wires (e.g., formed from a shape-memory polymer or metal) configured to move between a low surface area first configuration (e.g., delivery configuration) and a high sur- face area second configuration (e.g., deployed configura- tion). One or more silicone tubes may be attached to or extend around (e.g., encircle) all or some of wires compris- ing the framework. For example, once advanced from within the delivery needle and properly positioned within a hypoxic tumor (as discussed above), the gas exchange fluid 140 may be pumped/flowed from oxygenation element 120 through the first lumen 112 of the flexible elongate member 110 and through the silicone tubes of the gas exchange device 730. The gas exchange fluid 140 may return to the oxygenation element 120 through the second lumen 114 running through a center of the self-expanding stent framework and through the flexible elongate member 110. In various embodiments, the self-expanding stent framework may move to a variety of different second configurations, e.g., based on the size/ shape of the hypoxic tumor. All or a portion of the silicone tubes may be formed from or include a solid and oxygen permeable membrane to deliver/transfer oxygen from the gas exchange fluid 140 to the hypoxic tissue (as discussed above).

Referring to FIG. 8, in one embodiment, a gas exchange device 830 of the present disclosure may include a self- expanding stent framework comprising one or more wires (e.g., formed from a shape-memory polymer or metal) configured to move between a low surface area first con- figuration (e.g., delivery configuration) and a high surface area second configuration (e.g., deployed configuration). A silicone membrane may be formed on an inner and outer surface of the stent framework to define an open space therebetween such that the gas exchange fluid 140 may flow around the stent framework between the membranes. For example, once advanced from within the delivery needle and properly positioned adjacent to or within a hypoxic tissue (as discussed above), the gas exchange fluid 140 may be pumped/flowed from oxygenation element 120 through the first lumen 112 of the flexible elongate member 110 and between the inner and outer membranes of the gas exchange device 830. The gas exchange fluid 140 may return to the oxygenation element 120 through a center of the gas exchange device 830 and through the second lumen 114 of the flexible elongate member 110. All or a portion of the inner and/or outer membranes may be formed from or include a solid and oxygen permeable portion to deliver/ transfer oxygen from the gas exchange fluid 140 to the hypoxic tissue (as discussed above).

Figure 9C:
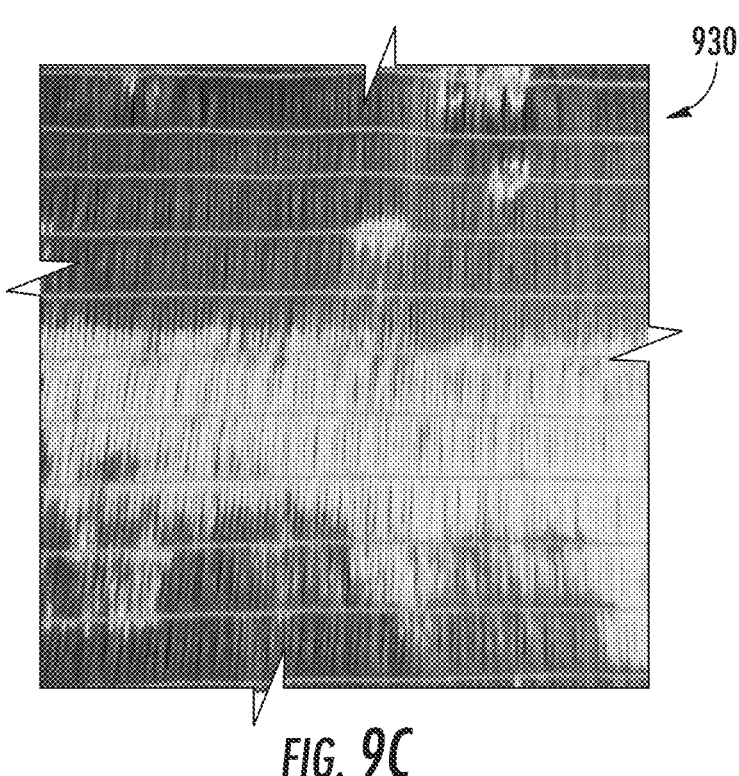

Referring to FIGS. 9A-9C, in one embodiment, a gas exchange device 930 of the present disclosure may include a plurality of interconnected tubes woven into a sheet (FIG. 9C) configured to move between a low surface area first configuration (e.g., delivery configuration; FIG. 9A) and a high surface area second configuration (e.g., deployed con- figuration; FIG. 9B). For example, once advanced from within the delivery needle and properly positioned adjacent to a hypoxic tissue (as discussed above), the gas exchange fluid 140 may be pumped/flowed into the plurality of tubes through the first lumen 112 of the flexible elongate member 110 to inflate the interconnected tubes and unroll/unfurl the gas exchange device 930. In various embodiments, the unrolled gas exchange device 930 may cover/encircle the tumor. The gas exchange fluid 140 may return to the oxygenation element 120 through the second lumen 114 of the flexible elongate member 110. All or a portion of the interconnected tubes of the gas exchange device 930 may be formed from or include a solid and oxygen permeable membrane (e.g., silicone membrane, etc.) to deliver/transfer oxygen from the gas exchange fluid 140 to the hypoxic tissue (as discussed above).

Figure 10:
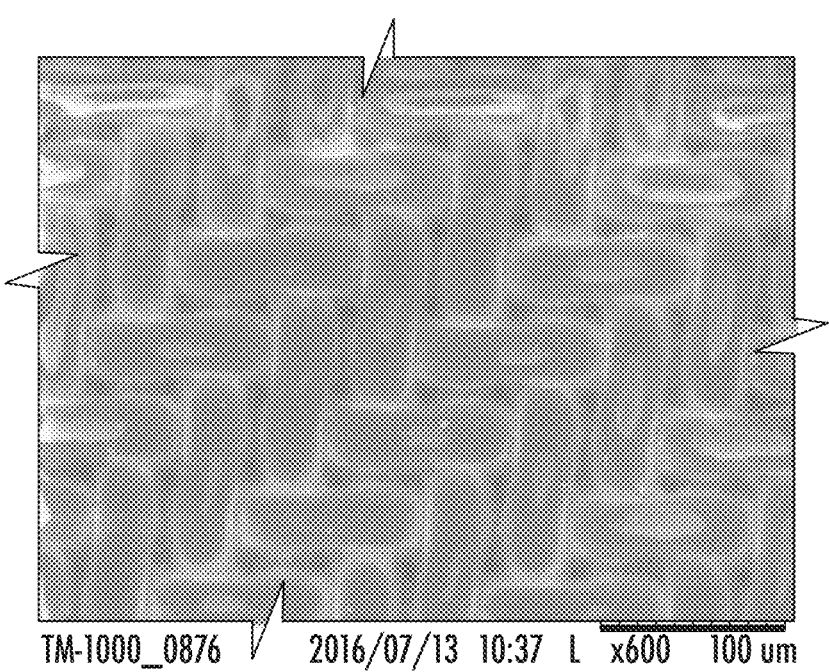
FIGS. 10-12 provide enlarged perspective views of various surfaces of gas exchange devices, according to various embodiments of the present disclosure.
Figure 11:
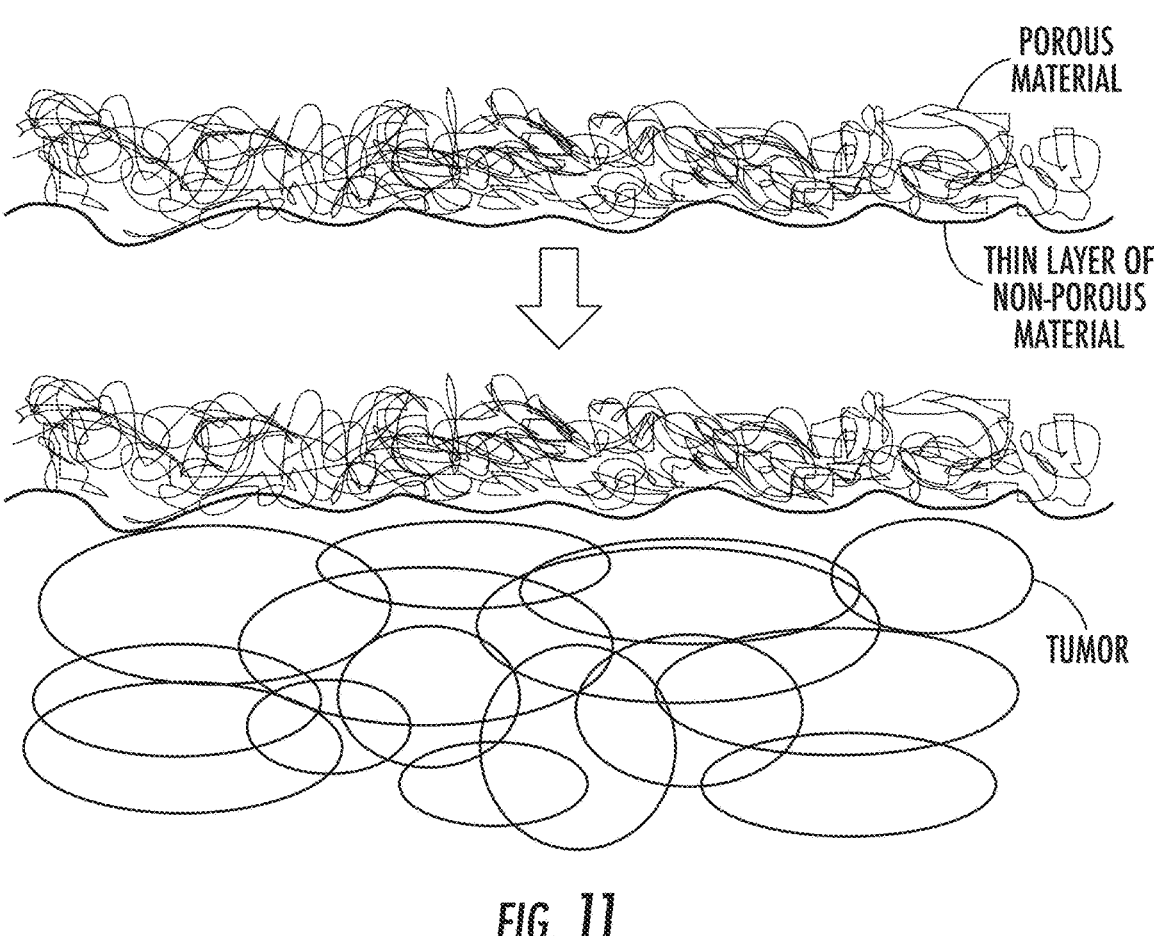
Figure 12:
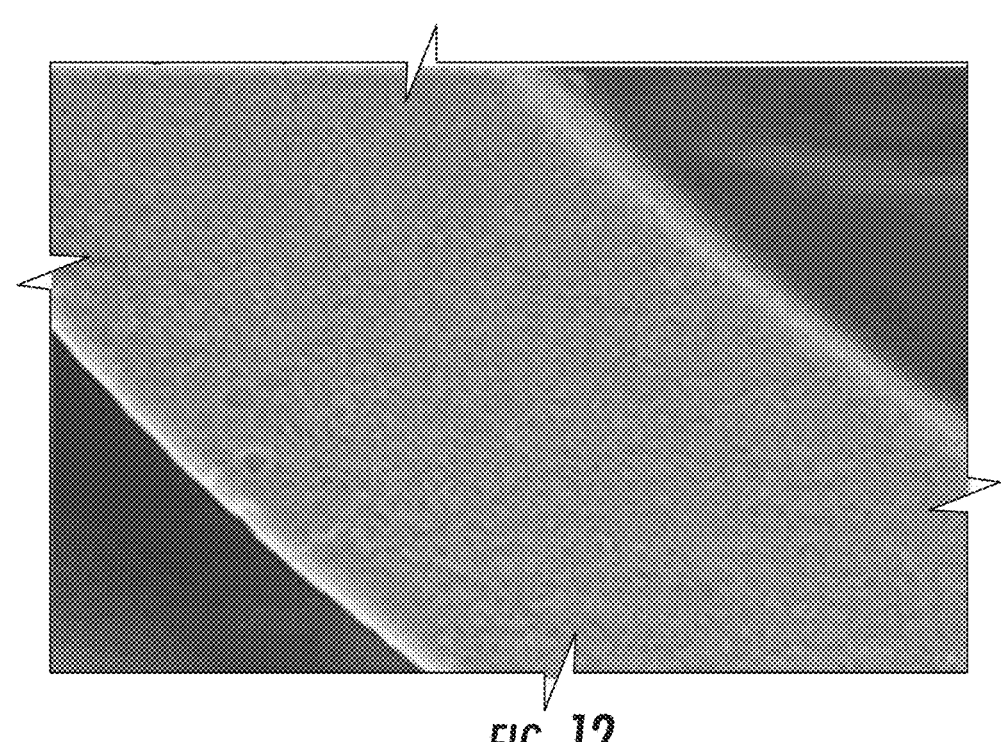

Referring to FIGS. 10 and 11, in one embodiment, the oxygen-permeable portion of a gas exchanged device 130, 230, 330, 430, 530, 630, 730, 830, 930 of the present disclosure may include a thin layer/sheet of a woven (FIG. 10) or electrospun (FIG. 11) polymer to provide a highly porous membrane. A thin layer of non-porous material may be applied (e.g., spray coated) onto one side of the woven or woven or electrospun sheet, e.g., the side of the gas exchange device through which oxygen will be delivered to the tumor. The thin layer of non-porous material may contact the tumor and the gas exchange fluid may contact the porous woven or electrospun membrane. In various embodiments, the thin layer of non-porous material may include the surface features (e.g., undulations, roughness, texture etc.) of the underlying woven or electrospun sheet to increase the surface area available for delivery of oxygen into the tumor. FIG. 12 provides a magnified view of a commercially available gas exchange material comprising a thin non- porous layer applied to a porous membrane support (e.g., Oxyphan™ 3M).

Although the present disclosure describes the oxygen- ation element as external to the patient with oxygen deliv- ered through inlet and outlet ports, in one embodiment the oxygenation may be implanted within the patient. For example, the oxygenation element 120 may be positioned within a well oxygenated blood source (e.g., the aorta) such that the gas exchange membrane 129 may retransfer oxygen from the high partial pressure blood of the aorta to the gas exchange fluid 140 for delivery through the first lumen 112 of flexible elongate member 110 to the gas exchange device 130 (as discussed above).

All of the devices and/or methods disclosed and claimed herein can be made and executed without undue experimen- tation in light of the present disclosure. While the devices and methods of this disclosure have been described in terms of preferred embodiments, it may be apparent to those of skill in the art that variations can be applied to the devices and/or methods and in the steps or in the sequence of steps of the method described herein without departing from the concept, spirit and scope of the disclosure. All such similar substitutes and modifications apparent to those skilled in the art are deemed to be within the spirit, scope and concept of the disclosure as defined by the appended claims.

What is claimed is:
1. A medical system, comprising:
a flexible elongate member;

an oxygenation element fluidly connected to a proximal end of the flexible elongate member;

a gas exchange device fluidly connected to a distal end of the flexible elongate member, the gas exchange device comprising an outer tubular member, an inner tubular member disposed within the outer tubular member, and a solid oxygen permeable membrane that is attached to and extends beyond a distal end of the outer tubular member, thereby forming an oxygen diffusing tip of the device, wherein an interior of the outer tubular member is fluidly connected to an interior of the solid oxygen permeable membrane, wherein an interior of the inner tubular member is fluidly connected to the interior of the solid oxygen permeable membrane, and wherein a distal end of the inner tubular member extends into the interior of the solid oxygen permeable membrane;

an ultrasonic transducer positioned within the interior of the solid oxygen permeable membrane;

a gas exchange fluid contained within the system and flowable from the oxygenation element to the gas exchange device through a first lumen of the flexible elongate member and flowable from the gas exchange device to the oxygenation element through a second lumen of the flexible elongate member; and a gas exchange membrane disposed within the oxygenation element, the gas exchange membrane configured to transfer oxygen to the gas exchange fluid.

2. The system of claim 1, wherein a proximal end of the first lumen is fluidly connected to a gas exchange fluid outlet port of the oxygenation element and a distal end of the first lumen is fluidly connected to the gas exchange device; and wherein a proximal end of the second lumen is fluidly connected to a gas exchange fluid inlet port of the oxygenation element and a distal end of the second lumen is fluidly connected to the gas exchange device.

3. The system of claim 1, wherein the oxygenation element includes an oxygen inlet port and an oxygen outlet port.

4. The system of claim 1, wherein the gas exchange device is configured to deliver oxygen from the gas exchange fluid to a hypoxic tumor of a patient.

5. The system of claim 1, wherein the first lumen of the flexible elongate member is configured to deliver the oxygenated gas exchange fluid from the oxygenation element to the gas exchange device.

6. The system of claim 1, wherein the second lumen of the flexible elongate member is configured to deliver the gas exchange fluid from the gas exchange device to the oxygenation element.

7. A method of tumor treatment using the medical system of claim 1, comprising:

positioning the gas exchange device within or adjacent to a hypoxic tumor of a patient;

delivering oxygen from the gas exchange device to the hypoxic tumor such that some or all of the cells of the hypoxic tumor become hyperoxic; and irradiating the tumor.

8. The method of claim 7, further comprising, prior to positioning the gas exchange device, identifying one or more hypoxic regions of the tumor.

9. The method of claim 8, wherein the hypoxic region is identified using magnetic resonance imaging.

10. The method of claim 7, further comprising cooling the gas exchange device while delivering oxygen to the hypoxic tumor.

11. The method of claim 7, further comprising removing the gas exchange device from the patient after irradiating the tumor.

12. The method of claim 7, further comprising delivering another dose of oxygen from the gas exchange device to the tumor and irradiating the tumor a second time.

13. The system of claim 1, wherein the gas exchange device further comprises an outer sheath having porous sides and an open or closed distal end.

14. The system of claim 1, wherein the system comprises a plurality said gas exchange devices.

15. The system of claim 1, wherein the solid oxygen permeable membrane is adhered to an outer surface of the outer tubular member.

16. A medical system, comprising:

a flexible elongate member;

an oxygenation element fluidly connected to a proximal end of the flexible elongate member;

a gas exchange device fluidly connected to a distal end of the flexible elongate member, the gas exchange device comprising an outer tubular member, an inner tubular member disposed within the outer tubular member, and a solid oxygen permeable membrane that is attached to and extends beyond a distal end of the outer tubular member, thereby forming an oxygen diffusing tip of the device, an interior of the outer tubular member fluidly connected to an interior of the solid oxygen permeable membrane, and an interior of the inner tubular member fluidly connected to the interior of the solid oxygen permeable membrane;

a tubular outer sheath having a porous distal end and an open or closed distal tip, the oxygen diffusing tip configured to be disposed within the tubular outer sheath adjacent the porous distal end;

a gas exchange fluid contained within the system and flowable from the oxygenation element to the gas exchange device through a first lumen of the flexible elongate member and flowable from the gas exchange device to the oxygenation element through a second lumen of the flexible elongate member; and a gas exchange membrane disposed within the oxygenation element, the gas exchange membrane configured to transfer oxygen to the gas exchange fluid;

wherein the tubular outer sheath is configured to be retracted relative to the oxygen diffusing tip, thereby exposing the oxygen diffusing tip; and wherein a distal end of the inner tubular member extends into the interior of the solid oxygen permeable membrane and wherein an ultrasonic transducer is positioned adjacent an outer surface of the tubular inner sheath.

17. The system of claim 16, wherein the porous distal end of the tubular outer sheath contains a plurality of apertures.

18. The system of claim 16, wherein the tubular outer sheath has an open distal tip.

19. The system of claim 16, wherein the distal tip is a sharp distal tip.

20. A medical system, comprising:

a flexible elongate member;

an oxygenation element fluidly connected to a proximal end of the flexible elongate member;

a gas exchange device fluidly connected to a distal end of the flexible elongate member, the gas exchange device comprising an outer tubular member, an inner tubular member disposed within the outer tubular member, and a solid oxygen permeable membrane that is disposed at a distal end of the outer tubular member, thereby forming an oxygen diffusing tip of the device, an interior of the outer tubular member fluidly connected to an interior of the solid oxygen permeable membrane, and an interior of the inner tubular member fluidly connected to the interior of the solid oxygen permeable membrane;

an ultrasonic transducer positioned within the interior of the solid oxygen permeable membrane;

a gas exchange fluid contained within the system and flowable from the oxygenation element to the gas exchange device through a first lumen of the flexible elongate member and flowable from the gas exchange device to the oxygenation element through a second lumen of the flexible elongate member; and a gas exchange membrane disposed within the oxygenation element, the gas exchange membrane configured to transfer oxygen to the gas exchange fluid.

* * * * *